United States Patent [19]

Carter

[11] 4,066,362

[45] Jan. 3, 1978

[54] APPARATUS AND METHOD FOR PERFORMING PHOTOMETRIC ANALYSIS

[75] Inventor: Elbert P. Carter, Wilmington, Del.

[73] Assignee: E. I. Du Pont de Nemours and Company, Wilmington, Del.

[21] Appl. No.: 753,200

[22] Filed: Aug. 16, 1968

[51] Int. Cl.² .................... G01N 33/16; G01N 21/24
[52] U.S. Cl. ............................. 356/180; 23/253 R; 23/230 B; 356/201; 356/246
[58] Field of Search ............ 250/218; 356/208, 39–42, 356/197, 198, 240, 180, 246

[56] References Cited

U.S. PATENT DOCUMENTS

| 2,442,462 | 6/1948 | Kirschbaum | 356/41 |
| 2,706,927 | 4/1955 | Wood | 250/218 X |
| 3,152,587 | 10/1964 | Ullrich et al. | 356/41 X |
| 3,286,583 | 11/1966 | Ferrari | 250/218 X |
| 3,415,997 | 12/1968 | Vinzelberg et al. | 356/197 |

Primary Examiner—R.E. Serwin

[57] ABSTRACT

An apparatus and method for photometrically analyzing a fluid in which the fluid is deposited in a deformable container, the container is squeezed between two windows to form a sample cell with a precise cell length, and then the optical density of the fluid in the container is measured with a photometer. The cell forming means is designed such that the majority of the fluid in the deformable container is forced into the sample cell so that the dimensions of the sample cell can be maximized for the small amount of fluid contained in the container. A means for coating the interfaces between the sample cell and the windows may also be provided so that changes in reflection from the surface of the deformable container due to imperfections in that surface are minimized.

14 Claims, 4 Drawing Figures

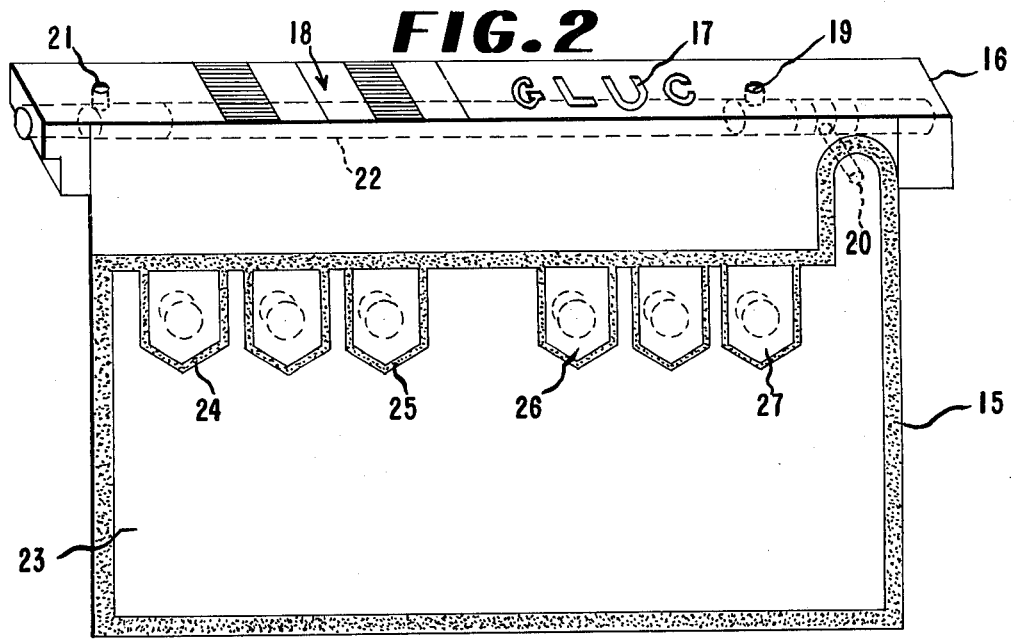
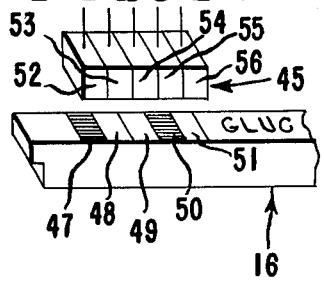
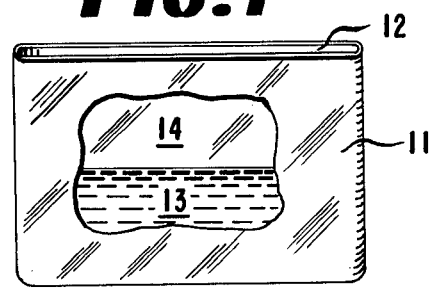
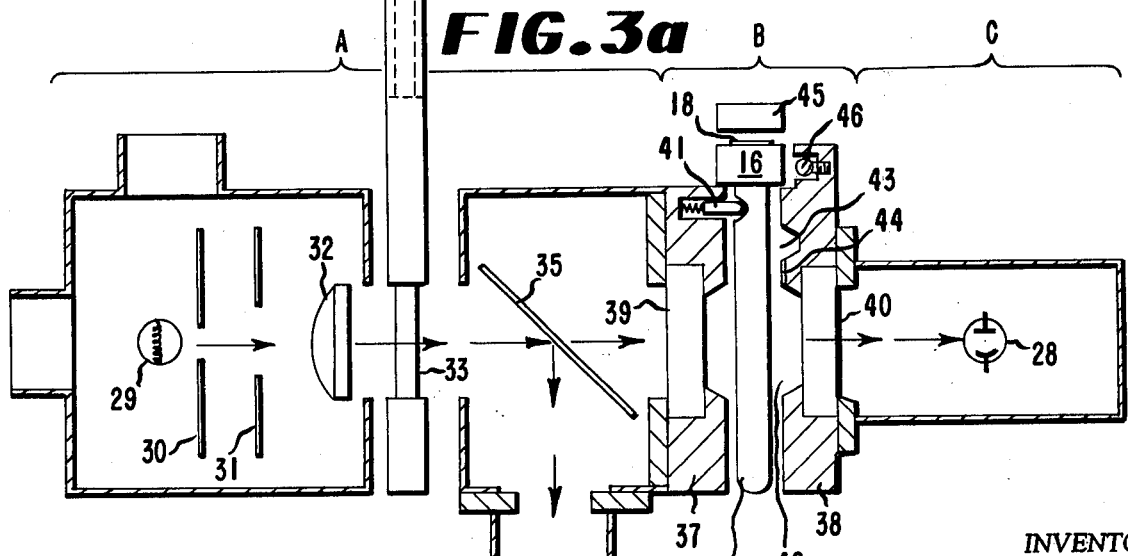

APPARATUS AND METHOD FOR PERFORMING PHOTOMETRIC ANALYSIS

CROSS REFERENCES TO RELATED APPLICATIONS

This invention is particularly related to the subject matter of application Ser. No. 545,494 filed on 4/26/66 entitled Analytic Test Pack and Process for Analysis by D. R. Johnson et al (assigned to the assignee of the present application), in that the Analytic Test Pack described and claimed therein may be used to provide the sample cell of the instant invention. It is also related to the subject matter of application Ser. No. 753,197 filed on the same day as this invention entitled Analytic Clinical Analayzer by inventors E. P. Carter, et al (assigned to the assignee of the present application), in that the instant invention may be used in the system described and claimed therein to perform the photometric analysis on the test solution. These cross references are merely intended to illustrate and are not to restrict the scope and/or use of any of these inventions.

BACKGROUND

Photometric means have been used to perform chemical analysis on fluids for many years. Indeed photometers have now become an integral part of most chemical analysis equipment; particularly automatic analytic equipment. These instruments use various means to isolate the test sample into a specific region for measurement. Usually a rigid container called a cuvette, which is transparent to radiation within the frequency range required for the analysis, is used. The cuvette is subjected to radiation and the intensity of the radiation transmitted through the cuvette is monitored by a photocell.

One of the main advantages of an automatic instrument is in the reproducibility of its results. Yet the use of a cuvette into which the fluid to be sampled, buffer solutions, and necessary reagents are deposited, introduces possibilities of error and contamination which limit the reproducibility of results obtained from such instruments. There are a number of reasons for this. First, not only must the sample fluid and buffer solution be introduced into the cuvette while it is in the instrument, but also all the reagents used in the analysis must be introduced at that time. The more fluids that must be transferred by the instrument, the greater the possibility of error and of contamination. Second, the cuvette and the sample fluid contained in it are normally identified only by the fact that the cuvettes are kept in register throughout the instrument. While this is generally sufficient for the operation of the instrument, a positive identification is much to be preferred, especially when such an identification can be used to control the operation of the instrument. Third, a cuvette is usually open to the air and, therefore, susceptible to contamination. Even if this problem is overcome, the cuvette has to be cleaned after each use or the next samples deposited in it will become contaminated. This is an expensive and time consuming procedure which could profitably be eliminated. Finally, the use of a cuvette is a very inefficient way to utilize sample fluid since more fluid than is actually necessary for the analysis must be deposited in the cuvette.

Most of these problems can be overcome if, instead of using a cuvette, a deformable container such as that used in the Analytic Test Pack described and claimed in application Ser. No. 545,494 is used. In this pack, the reagents are prepackaged in this container so that only the sample fluid and necessary buffer solution need be transferred to the pack when it is in the instrument. The container is completely closed and disposable so that the probability of contamination is kept to a minimum, and cleaning is unnecessary. In addition, the test to be run can be positively identified on the container, and this identification can be used to program the operation of the instrument at each stage of the analysis.

The use of a deformable container, however, still leaves the problem of using the fluid within the container most efficiently. In order to have a reproducible photometric analysis of the fluid contained in the sample cell, some means must be provided for insuring that the length of the sample cell presented to the photometer is the same in each case. This length should be maximized, since the sensitivity of a photometer is directly proportional to the length of the path which the light takes through the sample. In addition, in the case of a sample cell made from a film, the area of the sample cell presented to the photometer should also be maximized so that the effect of reflection from imperfections in the surface of the film can be minimized. Competing with the advantage of maximizing the dimensions of the sample cells are the advantages realized from minimizing the amount of fluid contained in the sample cell. This is important both from the point of view of cost, if the amount of reagent required is reduced, and in those cases where there is very little sample fluid available.

SUMMARY OF INVENTION

The subject matter of the present invention is a novel apparatus and method for performing photometric analysis on a fluid contained in a deformable container. In this invention, a specific amount of sample fluid and buffer solution are first deposited in the deformable container, which is then sealed at the top by pressing the pack between sealing bars. All of the fluid in the pack is thus restricted to a small pouch at the bottom of the container. This pouch is then squeezed between two jaws containing recessed windows. The fluid in the pouch hydraulically deforms the sides of the pouch into the contour of the recess formed between the two jaws. Since the jaws are brought together until only the thickness of the plastic pouch separates them, except in the region of the recess, the majority of the fluid contained in the deformable container is forced into the recess. In this way, a sample cell of precise and reproducible dimensions is formed. In order to insure that the same amount of fluid is contained in the sample cell each time it is formed, a pressure relief chamber is provided.

Optionally, a contact fluid applicator can be provided. The film, from which the deformable container is made, generally contains imperfections which trap air between the windows and the film. There is reflection from the surfaces of these air bubbles. If the size and shape of the air bubbles remains constant, they provide a constant error for which compensation can be made. Under constant pressure from the jaws, however, the film flows so that the size and shape of the air bubbles change, introducing a variable error for which it is difficult if not impossible to compensate. To circumvent this problem, a contact fluid can be applied to the deformable container. The imperfections in the film still remain, but instead of being surrounded by air they are now surrounded by a fluid which inhibits the flow of the film, and decreases the difference in the indexes of refraction at the interface. Reflection from film imperfections then becomes a tolerable constant error.

Specifically, the apparatus comprises: a deformable container; a cell forming means adapted to form the deformable container into a sample cell with flat sides; an irradiating means; and a measurement photocell. The cell forming means is further adapted to place said cell in the optical path between said irradiating means and said photocell. The method comprises: placing a fluid in a deformable container; forming the container into a sample cell by squeezing it between two flat windows; wetting the interface between the container and the windows with a contact fluid to reduce flow in the film and improve optical contact; then subjecting the sample cell to radiation of fixed intensity and distinct but variable frequency, and measuring photometrically the intensity of the transmitted radiation.

The operation of the present invention can best be illustrated with reference to the following figures, wherein:

FIG. 1 is one embodiment of a deformable container that can be used in this invention;

FIG. 2 is another embodiment of a deformable container that can be used in this invention; and FIG. 3 is a schematic diagram of one embodiment of the present invention.

DISCUSSION OF THE DRAWINGS

FIG. 1 is an illustration of one of the simplest embodiments of the deformable container used in this invention. The container itself 11 can be made from any transparent deformable material, but it is usually a pliable polymeric material, preferably selected from any of the following materials: polymers of olefins, e.g., ethylene, propylene and copolymers with vinyl acetate, etc.; halogenated polymers, e.g., polymers of vinyl acetate, rubber hydrochloride, vinyl fluoride polymers, etc.; polyesters, e.g., polyethylene terephthalate, ionomer resins, etc.; or laminate thereof. The word transparent means transparent to the particular radiation employed in the photometric device. In most usual applications, this means that the container should be made from a material transparent to ultraviolet radiation as well as visible light, since many of the analyses performed use ultraviolet light. The container shown in FIG. 1 is a sack with an opening 12, through which the fluid to be tested 13 can be introduced. Usually, the container 11 is only partially filled, so that there is an air space 14 above the fluid, but it is advantageous to keep the size of this air space to a minimum.

A more sophisticated design of the deformable container, which is the subject of application Ser. No. 545,494 noted above, is illustrated in FIG. 2. This container comprises a deformable pouch 15, made from some pliable polymeric material such as Surlyn ®, and a header 16 made from a non deformable material. This header may, optionally, contain some identification symbols 17, for visual identification, and some identification marks 18 which can be read and decoded photometrically. These identification marks 18 are useful not only to identify the test but also as a means of programming the operation of the instrument, as will be shown below. Optionally, the identification marks can be raised portions of the header which can be decoded mechanically; or any other suitable identification marks. The header also contains an opening 19, through which the fluid to be analyzed can be introduced into the deformable pouch through inlet 20. Alternatively, the fluid to be analyzed may be introduced through the opening 21 so that it passes through a separation column 22 before entering the pouch at 20. The separation column can be an ion exchange column, a filter, or any other device needed in the analysis. The deformable pouch 15 is composed of a reaction chamber 23 and a number of dimples 24, 25, 26 and 27, separated from the reaction chamber by rupturable seals. The dimples contain reagents which can be introduced into the reaction chamber at will, by merely rupturing those seals.

The two described embodiments of the deformable container are only illustrative of the possible simplicity or complexity of the container, and are not meant to be restrictive.

FIG. 3a is a schematic diagram of one embodiment of the photometer itself. It comprises an irradiating means, A, a cell forming means, B, and a measurement means, C. In this embodiment, the measurement means, C, is a measurement photocell 28, of any design suitable for the purpose, which is responsive to visible, ultraviolet, and near infrared radiation. However, any detection means responsive to the particular radiation can be used. The essential part of the irradiating means, A, is an irradiation source. In this embodiment it is a suitable lamp 29, such as a quartz iodine lamp. The lamp should give a reasonable intensity of radiation over the frequency range desired. Optionally, any other source of radiation for producing the frequency of radiation required in the analysis can be used. The light may be collimated, by collimators 30 and 31, and focused by lens 32. The desired frequency is selected by passing the light through a filter 33. This filter can be variable. One simple way of making it variable is to have a plurality of filters in a filter wheel 34 which can be rotated, either automatically or manually, until the desired filter is in place.

Since the intensity of the radiation will vary as a function of frequency, it is desirable, but not necessary to include some device to maintain a constant intensity at the sample, no matter what the frequency might be. One way of accomplishing this is to use a beam splitter 35 and a regulating photocell 36. The beam splitter can be a partially silvered mirror which transmits a portion of the light incident on it, and reflects the rest. Usually such mirrors transmit 90 percent of the radiation and reflect 10 percent, but any reasonable ratio is suitable. The reflected beam is then made incident on the regulator photocell 36 so that any variation in the intensity of the light that arrives at the mirror will be detected by the photocell. By means of conventional feedback circuitry, such as that shown in Malmstadt, Enke, and Toren Electronics for Scientists, at page 371, this information can be fed to the power supply of the lamp 29, and the amount of power supplied to the lamp can be varied to compensate for the variation.

Since any interruption of the beam of light would cause the regulating photocell to increase the power to the lamp to the point of destruction, some sort of voltage clamp circuit must be included. This limits the power to the lamp to within reasonable limits. Such circuits designed to supply a fixed input voltage to the power source for lamp 29 when the signal to photocell 36 is interrupted, so that the power source will not react as if the lamp 29 were not receiving power and supplying a surge of power to the lamp, are well known to those skilled in the art. A circuit such as that shown in Malmstadt et al. at page 414 would suffice.

The irradiating means, A, and measurement means, C, are necessary and indispensable features of any photometer; well known to those skilled in the art. The critical feature of the present invention lies in the cell-forming means, which adapts the photometer for use with a deformable sample container in a way such that the most effective use is made of sample fluid in that container. The cell-forming means comprises a pair of movable jaws 37 and 38, into which a pair of windows 39 and 40 are recessed. In this embodiment, the windows are flat windows made from quartz or any other suitable material. When the container is inserted between the movable jaws, and the jaws are closed, the container is first sealed at the top by some means such as a sealing bar 41. This sealing bar performs two functions. First, it acts to squeeze all of the fluid contained in the upper portion of the sample container, including the dimples of the test pack shown in FIG. 2, into the bottom of the sample container. This is important if the majority of the fluid in the sample container is to be utilized. Second, the sealing bar acts to seal off the sample container so that the bottom of the sample container forms a sealed pouch containing the majority of the fluid which was deposited in the sample container. The seal is made below the dimples, if any are present, to avoid deformed film near the ruptured seals. The seal closes off the pouch at the bottom of the test container so that when pressure is exerted on this pouch none of the fluid contained in it will escape.

As the jaws close further, the fluid trapped in the sealed pouch hydraulically deforms the plastic walls of the pouch into the contour of the chamber 42 between the windows. This is an important step in the procedure, since all of the fluid contained in the bottom of the pouch must be forced into a sample cell with precise and reproducible dimensions. The most critical dimension is the length of the sample cell. If this length is not reproducible upon forming and reforming the cell, then measurements made by the photometer would not be reproducible, and the system would be self-defeating. In this embodiment, the jaws of the cell-forming means are brought together so that only the thickness of the film which makes up the wall of the deformable container separates them, except in the region of the recess 42. In this embodiment, the jaws exert a pressure of approximately 100 psi on the pouch, forcing the fluid into the area of the recess.

In one embodiment the sample container is filled with exactly 5.0 ml. of fluid, and the recess is designed to form a sample cell which is exactly 1.0 cm. in length and 2.0 cm. in diameter at the window. The cell broadens slightly at the center, so that the sample cell will hold approximately 3.8 ml. of fluid. There is some fluid trapped in other parts of the system. The amount of fluid trapped will vary from container to container. Hence, if the only recess in the jaws was the one that formed the sample cell, variations in the amount of trapped fluid would cause variations in the separation of the jaws and consequently in the length of the sample cell. To avoid this variation, a pressure relief chamber 43 is included, and connected to the cell-forming chamber 42 by a narrow channel 44. The excess fluid, which could cause variations in cell length, is then deposited in the relief chamber, so that in this embodiment the length of the sample cell is reproducible to within 0.25 percent.

The deformable container is forced into the contours of the depression in the movable jaws. Since the walls of this depression are made from flat quartz plates, the surface of the container becomes flat. The problem of reflection at the film-air-quartz interface still remains, however. Films generally contain imperfections, and these imperfections cause air bubbles to be formed between the film and the windows. There are two surfaces of the air bubble from which reflection can take place. This in itself would not be of too much concern if the size and shape of the air bubbles remained constant. In such a case the error would be constant, and the area of the sample cell presented to the radiation could be made large enough so that the constant error is small. Under the constant pressure from the jaws, however, the film flows and the size and shape of the air bubbles change, introducing a variable error. To circumvent this problem, a contact fluid-injecting means, can be included. One way to inject contact fluid would be to provide input conduits 57 and 58 and outlet conduits 59 and 60 in jaws 37 and 38, respectively, so that contact fluid can be inserted into the space between the sample container and the windows through conduit 57 and 58, and excess fluid can be drained out through conduits 59 and 60. The device merely deposits a contact fluid, such as water, on the surface of the deformable container so that the space between the sample container and the windows, in the region of the film imperfection, is filled with the contact fluid rather than with air. This inhibits changes in the dimension of the area around the flaw and, at the very least, converts the variable error to a constant error. Actually, the contact fluid also improves optical contact between the windows and the sample container, so that the amount of reflection is decreased. In this embodiment, stray light into the photocell is less than 0.01 percent of the normal beam intensity after filtering.

One of the main advantages of performing analysis in a sealed container is that the analysis can be performed automatically and continuously without fear of contamination. To facilitate this continuous operation, the container of FIG. 2 has an identification code 18 on its header 16. If the analytic instrument is designed properly, presentation of this code at various stages in the operation will program the instrument as to the steps which it must follow. Such an instrument with complex logic and programming stages is the subject of patent application Ser No. 753,197. For purposes of this invention, it is enough to note that the photometer of FIG. 3 can, optionally, include an identification means, 45 which is positioned above the header of the deformable container when the container is in the proper position within the photometer. FIG. 3b is an enlarged view of that portion of FIG. 3a which includes the header of the deformable container and the identification means.

In this figure, the header has a five space identification mark on it, and the identification means is a set of five photodiodes. Light from a lamp 46 in FIG. 3a is reflected through the header into the photodiodes, through the identification code. In this case, where there are two dark spaces 47 and 50, and three blank spaces 48, 49 and 51, the light reaching the photodiodes 52 and 55 is less intense than the light reaching photodiodes 53, 54 and 55 through the unoccupied identification spaces. The pattern detected by the photodiodes identifies the sample, and a signal corresponding to this identification is sent to the programming section of the machine which determines what steps the photometer system is to take. The identification means can be a simple dark-light identification or it can be a sophisticated character recognition identification means, depending on the needs of the particular device.

In the operation of this particular photometer, the first step is the closing of jaws 37 and 38, sealing off the container 15 by means of the sealing bar 41. As the jaws close tightly, the fluid forces the container into the shape of the cell-forming region. Contact fluid is sprayed on the interface between the windows 39 and 40 and the container. By the time the jaws have closed, a sample cell has been formed which is in optical contact with two flat windows. Excess fluid is forced into the pressure relief chamber, so that a sample cell with precise dimensions is formed. Usually, this step leaves the fluid in a turbulent state, and it is best to allow this turbulence to subside. Fifteen seconds is generally enough time for this to occur. While the turbulence is subsiding, the identification means has identified the test to be run, the proper frequency of radiation is chosen by rotating the filter wheel until the proper filter is in place, and the regulating photocell has adjusted the power supplied to the radiation source so that the intensity of the light passing through the filter is maintained at the operative level. When the turbulence has subsided, the measurement photocell measures transmission for a short time interval (about 1 sec.) then waits for a time interval (about 17 sec.) before it makes a second measure of transmission.

The difference in transmission is the output of the photometer. This difference can either be read directly, displayed by some conventional means, or sent to the logic and programming stages of an analyzing instrument, as described in application Ser. No. 753,197, to be interpreted and indexed with other information about the particular test.

The procedure described in the preceeding paragraphs is intended to illustrate how the invention described herein can be adapted for use in sophisticated analytic equipment. It is not meant to indicate that the use of such a photometer is restricted to such instruments. This invention is applicable in the simplest case where a deformable test pack is to be used. The details above are merely intended to indicate to those skilled in the art the versatility of such a device.

What is claimed is:

1. An apparatus for performing photometric analysis on a sample fluid contained in a deformable container, comprising: an irradiating means, said deformable container being transparent to the radiation from said irradiating means; a cell-forming means adapted to form said deformable container into a sample cell with a predetermined cell length, said cell-forming means comprising a sealing means adapted to squeeze the majority of said sample fluid into a region of said deformable container and to seal off that region to form a closed test pouch; and a radiation detection means adapted to measure the radiation transmitted through said sample cell.

2. The apparatus of claim 1 wherein said cell-forming means further comprises a pair of movable jaws and a pair of precisely positioned windows transparent to the radiation from said irradiating means and recessed into said movable jaws in such manner as to form a cell-forming chamber; said movable jaws being adapted to deform a portion of said test pouch into a sample cell, disposed substantially within the path of the radiation from said irradiating means, whose cell length is determined by the separation of said windows, and adapted so that the majority of the fluid contained in the test pouch will be forced into said sample cell.

3. The apparatus of claim 2 wherein the cell-forming means further comprises a narrow channel and a pressure relief chamber connected to said cell-forming chamber by said narrow channel; said pressure relief chamber being adapted in such manner that small variations in pressure exerted by the movable jaws on said test pouch and in the amount of fluid in said deformable container will not affect the length of said sample cell.

4. The apparatus of claim 2 wherein said cell-forming means further comprises a contact fluid and a contact fluid injecting means adapted to inject said contact fluid between said flat windows and the deformable walls of said test pouch.

5. The apparatus of claim 4 wherein said contact fluid is water.

6. An apparatus for performing photometric analysis on a sample fluid contained in a deformable container comprising: an irradiating means comprises, a source of radiation, a power supply for said source of radiation, a means for selecting the frequency of the radiation from said source of radiation, and a regulating means adapted to regulate the intensity of the radiation from said source of radiation, said deformable container being transparent to the radiation from said radiation means; a cell-forming means adapted to form said deformable container into a sample cell with a predetermined cell length; and a radiation detection means adapted to measure the radiation transmitted through said sample cell.

7. The apparatus of claim 6 wherein said means for selecting the frequency of the radiation from said source of radiation is an optical filtering means; and a regulating means; and said regulating means comprises a beam splitting means, a regulating photocell, and a feedback network connecting said regulating photocell to said radiation source; said beam splitting means being adapted to transmit a portion of the radiation from said radiation source to said sample cell and to reflect the rest of the radiation from said radiation source to said regulating means; and said beam splitting means and said regulating means being adapted so that variations in the intensity of the radiation arriving at said beam splitting means can be monitored by said regulating photocell, and fed back to the power supply for said source of radiation through said feedback network in such manner that the intensity of said radiation source can be varied to compensate for said variations.

8. The apparatus of claim 7 wherein said regulating means further comprises a voltage clamp circuit adapted to clamp the voltage supplied to the radiation source at a level which will not damage said source when the beam of light monitored by said regulating photocell is interrupted.

9. The apparatus of claim 1 wherein said deformable container comprises a deformable sack and a header, with identification marks, adapted to receive said sample fluid and to transmit said fluid to said deformable sack; and which further comprises an identification means and a programming circuit adapted to control the operation of said photometer system said identification means being adapted to decode the identification symbols on the header of said deformable container and to transmit this information to said programming circuit.

10. A method for measuring chemical changes in a fluid with a photometer which comprises: placing said fluid in a deformable container; sealing said container in such manner that a closed test pouch containing the majority of said fluid is formed; forming said test pouch into a sample cell, containing the majority of said fluid and disposed substantially within the path of radiation from an irradiating means, by squeezing it between two windows; subjecting said sample cell to radiation of fixed intensity and distinct but selectable frequency; and measuring photometrically the intensity of the transmitted radiation.

11. The method of claim 10 which further comprises wetting the surfaces of said test pouch which are in contact with said windows with a contact fluid.

12. The apparatus of claim 1 wherein said radiation detection means is a photocell.

13. Photometric means for monitoring the chemical composition of a reaction mixture held within a reaction compartment of a flexible disposable chemical testing container comprising radiation source means adjacent a first side of the reaction compartment, means adjacent the opposite side of the reaction compartment responsive to the magnitude of light absorbed by the reaction mixture as electromagnetic radiation is transmitted therethrough from said radiation source means, and means to press said radiation source means and said responsive means against opposite sides of the reaction compartment during analysis to define a fixed optical path length through the reaction mixture.

14. Photometric means for monitoring the chemical composition of a reaction mixture held within a reaction compartment of a flexible disposable chemical testing container comprising radiation source means adjacent a first side of the reaction compartment, means adjacent the opposite side of the reaction compartment responsive to the magnitude of light absorbed by the reaction mixture as electromagnetic radiation is transmitted therethrough from said radiation source means, and means to deform the flexible wall or walls of the reaction compartment, during analysis, to define a fixed optical path length through the reaction contained therein.

* * * * *